United States Patent [19]

McGregor et al.

[11] Patent Number: 5,079,234
[45] Date of Patent: Jan. 7, 1992

[54] INHIBITORS OF AMINOGLYCOSIDE NEPHROTOXICITY

[75] Inventors: Donald N. McGregor, Clinton, Conn.; Thomas J. Davidson, Liverpool, N.Y.

[73] Assignee: Bristol-Myers Squibb Co., New York, N.Y.

[21] Appl. No.: 327,645

[22] Filed: Mar. 23, 1989

[51] Int. Cl.$^5$ .............................................. A61K 31/71
[52] U.S. Cl. .................. 424/78.31; 514/789; 514/42; 514/974; 514/40; 536/13.4; 536/13.6; 536/13.7; 536/14; 536/16.8
[58] Field of Search ............... 424/81, 78, 79, 501; 514/40, 42, 974, 789, 974; 536/13.6, 13.4, 13.7, 14, 16.8

[56] References Cited

U.S. PATENT DOCUMENTS

| | | | |
|---|---|---|---|
| 3,928,583 | 12/1975 | Furuno et al. | 514/210 |
| 3,962,429 | 6/1976 | Furuno et al. | 514/40 |
| 4,110,439 | 8/1978 | Cooper et al. | 514/40 |
| 4,312,859 | 1/1982 | Petersen et al. | 514/40 |
| 4,526,888 | 7/1985 | Williams et al. | 514/12 |
| 4,654,325 | 3/1987 | Selenka et al. | 514/42 |
| 4,757,066 | 7/1988 | Shiokari et al. | 514/210 |
| 4,758,551 | 7/1988 | Meister et al. | 514/18 |
| 4,855,287 | 8/1989 | Watanabe et al. | 514/40 |

FOREIGN PATENT DOCUMENTS 8804925 7/1988 World Int. Prop. O. .

OTHER PUBLICATIONS

6th Edition of "Drug Evaluations", AMA and W. B. Saunders Co., Philadelphia, Pa., pp. 1433-1435 (1986) (1/18).

*Primary Examiner*—Ronald W. Griffin
*Attorney, Agent, or Firm*—Richard P. Ryan

[57] ABSTRACT

Certain water-soluble polyanionic organic acid polymers in the weight range of from about 1,000 to 30,000 daltons may be use to inhibit aminoglycoside nephrotoxicity. These polyanionic polymers are homopolymers or copolymers comprised of monomers selected from acrylic, methacryclic, vinylsulfonic and maleic acids; and are in a pharmaceutically acceptable salt form.

16 Claims, No Drawings

INHIBITORS OF AMINOGLYCOSIDE NEPHROTOXICITY

FIELD OF THE INVENTION

The present invention is directed to the use of selected organic acid polymer protectants to inhibit the nephrotoxicity associated with the use of antibiotic aminoglycosides. The invention also covers pharmaceutical compositions comprising such protectants and aminoglycosides for clinical use when coadministration is desired.

BACKGROUND OF THE INVENTION

Aminoglycoside antibiotics have been in use following the isolation of Streptomycin, the first clinically useful aminoglycoside, in 1944. Although the aminoglycosides are particularly useful due to their rapid bactericidal action in infections by susceptible organisms, their use is limited to more severe, complicated infections because of ototoxic and nephrotoxic side-effects. For this reason the aminoglycosides are considered to have a low therapeutic/risk ratio compared to other antibiotics used systemically.

Nephrotoxic effects from aminoglycoside usage are well documented in the literature. A recent description of aminoglycoside adverse reactions and precautions may be found in the 6th Edition of "*Drug Evaluations*", AMA and W. B. Saunders Co., Philadelphia, PA, pp. 1433–1435 (1986).

Several substances have been reported to be useful in inhibiting aminoglycoside-induced renal damage, particularly amino acid derivatives.

Williams, et al., in U.S. Pat. No. 4,526,888 disclosed the use of certain neutral and anionic polyamino acids to reduce aminoglycoside-induced nephrotoxicity. The specific polyamino acids taught by Williams, et al., are asparagine and aspartic acid polymers.

Meister, et al., in U.S. Pat. No. 4,758,551 reported o-glutamyl amino acids to be nontoxic agents for use in combatting renal toxicity caused by nephrotoxic drugs. Shiokori, et al., in U.S. Pat. No. 4,757,066 disclosed the use of N-acylated amino acids in association with penem or carbapenem antibiotics to reduce renal toxicity caused by use of the antibiotic by itself. In WO 8804-925A (Tulane E. Fund Administration), biosynthetic precursors of oxidizable small peptides such as Glu-Cys or (Gly-Cys-S)$_2$ are among various agents reported to prevent the nephrotoxic effect of aminoglycosides.

Other agents, less related to the present invention, include inter alia D-glucarates (e.g. U.S. Pat. No. 3,928,583, 4,122,171) and amilioride (U.S. Pat. No. 4,654,325).

None of the above-listed substances or references would suggest the polymeric anionic agents of this invention which are not amino acid derivatives or acidic sugar derivatives.

SUMMARY OF THE INVENTION

The invention results from the discovery that administration of certain organic acid polyanionic polymers, in the molecular weight range from about 1000 to 50,000, comprised of certain monomeric organic acids, such as acrylic, methacrylic, vinylsulfonic and maleic acids, can prevent or reduce nephrotoxicity resulting from aminoglycoside antibiotic usage. Objectives of this invention then are to provide methods for prevention or reduction of aminoglycoside induced nephrotoxicity, as well as to provide pharmaceutical antibiotic compositions with lower nephrotoxicity than for the antibiotic agents alone.

DETAILED DESCRIPTION OF THE INVENTION

Research into aminoglycoside-induced nephrotoxicity has led to the discovery that polyanionic polymers of simple monomeric organic acids, such as acrylic, methacrylic, vinylsulfonic, and maleic acids, e.g. polyacrylic acid; when administered in water-soluble polyanionic salt form in conjunction with an antibiotic aminoglycoside regimen can reduce the nephrotoxicity of the aminoglycoside agent. By water-soluble polyanionic salt form is meant that some or all of the polymeric organic acid moieties, e.g. —COOH, —SO$_3$H; are neutralized with a suitable base such as NaOH, KOH, NH$_4$OH, etc. so that the resulting polyanionic polymer is water-soluble. These forms are also referred to herein as water-soluble polyanionic polymers or as water-soluble polyanionic organic acid polymers.

The aminoglycoside antibiotic which can be employed in conjunction with the nephrotoxicity inhibiting polymers of the invention is any aminoglycoside antibiotic. Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), streptomycin (Merck Index 9th ed. #8611/8612), paromomycin (Merck Index 9th ed. #6844), sisomicin (Merck Index 9th ed. #8292), isepamicin and netilmicin, all known in the art. The useful antibiotics include the several structural variants of the above compounds (e.g. kanamycin A, B and C; gentamicin A, $C_1$, $C_{1a}$, $C_2$ and D; neomycin B and C and the like).

All aminoglycoside antibiotics tested to date accumulate in renal tissue and possess a certain nephrotoxic potential [Luft et al., J. Inf. Dis., 138(4): 541–595 (1978)]. Thus, the present invention is useful with any aminoglycoside antibiotic. The free bases, as well as pharmaceutically acceptable acid addition salts of these aminoglycoside antibiotics, can be employed.

For the purpose of this disclosure, the terms "pharmaceutically acceptable acid addition salt" shall mean a mono or poly salt formed by the interaction of one molecule of the aminoglycoside antibiotic with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals.

The renal toxicity inhibitors conjointly used with the nephrotoxic aminoglycosides of this invention are water-soluble salt forms of polymers of polyacrylic acid, polymethacrylic acid, polyvinylsulfonic acid, or polymaleic acid, including homopolymers of each, copolymers with each other and pharmaceutically acceptable copolymers of polyacrylic acid, polymethacrylic acid, polyvinylsulfonic and/or polymaleic acid with lesser amounts of comonomers. The useful polyanionic polymers possess physical characteristics that provide the following prerequisite polymer properties:

water-soluble: all or a sufficient number of the organic acid moieties (e.g. carboxylate, sulfonate groups) are in ionic form due to salt formation with a water-soluble, pharmaceutically acception cation (Na+; K+; NH4+; and the like) so that the polymer is water-soluble. Not every organic acid moiety in the polymer need be in ionic salt form.

polyanionic (by virtue of ionized organic acid functional moieties, e.g. carboxylate and sulfonate;

small enough in size to pass through the glomerulus;

large enough to efficiently complex the aminoglycoside;

sufficiently stable (resistant to host metabolism).

Due to the polyanionic sites, the polymers are made water soluble by salt formation employing techniques known to those skilled in the art such as neutralization of the acidic functional groups with bases of pharmaceutically acceptable cations, e.g. sodium, potassium, ammonium, etc. It would be known to a practitioner skilled in the pharmaceutical arts that many other pharmaceutically acceptable cations can be selected for the polyanionic sites. In many instances, selection of the cation can influence stability, absorption, and the like, as would be evident to one in the art. In some instances not all the polyanionic sites need be in salt form. In these instances the acidic polymer may be substantially neutralized to a selected pH, e.g. about pH 7, using an appropriate base such as sodium hydroxide, potassium hydroxide, ammonium hydroxide, or the like.

The useful polymers have a molecular weight between about 1000 and about 50,000, and preferably between about 1000 and about 20,000.

The polymeric substances and aminoglycosides of the invention can be conjointly used in a variety of modes. Preferably, the aminoglycoside antibiotic and the inhibitory polymer are combined into a single dosage unit, preferably with a pharmaceutically acceptable carrier, for example, a cosolution or dispersion in an inert pharmaceutically acceptable solvent or dispersing agent or the like. Typically, pharmaceutically acceptable carriers can be any of those heretofore employed or compatible with the aminoglycoside antibiotic.

Alternatively, the inhibitory polymer can be separately formulated with pharmaceutically acceptable materials and administered separately; either concurrently with the aminoglycoside antibiotic or within about an hour before or after administration of the aminoglycoside antibiotic.

The mode of administration, the dosage and frequency of dosage is governed by the mode of administration and dosage considerations conventionally employed with the aminoglycoside antibiotic. Thus, for example, various of the combinations of the invention can be administered intramuscularly or intravenously, or otherwise, as dictated by medical and pharmacological practice related to the desired use of the particular antibiotic employed.

The amount of inhibitory polymer employed in conjunction with the aminoglycoside antibiotic is an aminoglycoside antibiotic nephrotoxicity reducing amount. The amount varies depending upon the aminoglycoside employed. Typically, the amount of inhibitory polymer employed is at least about 0.002 moles and preferably at least about 0.005 moles of the polymer per mole of the aminoglycoside antibiotic. The upper limit is also influenced by practical weight and cost considerations. Amounts as high as 10 moles of polymer per mole of antibiotic have been considered, but appear to be unnecessary as much lower levels appear to provide excellent inhibition. A preferred range of inhibitory polymer to aminoglycoside ratio is from about 0.01 to 2 moles of polymer per mole of antibiotic.

It may be seen then that by employing water-soluble polyanionic polymers of certain organic acid monomers, in a pharmaceutically acceptable salt form, the two objectives of the invention can be met.

1. A method for preventing or reducing nephrotoxicity of an aminoglycoside antibiotic is disclosed herein and comprises the administration of an effective dose of a water-soluble salt form of a polymer of molecular weight from about 1000 to about 50,000. The polymers are comprised of polymerized units of acrylic acid, methacrylic acid, polyvinylsulfonic acid, and maleic acid; either singly (homopolymer), mixed with another member (copolymer) or with lesser amounts of a pharmaceutically acceptable comonomer.

2. A second objective provides aminoglycoside compositions having reduced nephrotoxicity as a result of incorporation of the nephrotoxicity-inhibiting polymers of the present invention. These pharmaceutical compositions comprise antibiotic-effective amounts of aminoglycosides, effective nephrotoxicity-inhibiting amounts of polymers as described herein, and pharmaceutically acceptable carriers and/or vehicles which would be familiar to one skilled in the pharmaceutical arts. The actual amounts of aminoglycosides employed will range from those given in standard references for prescription drugs, e.g. "Physicians Desk Reference", 42nd Edition (1988); "Drug Evaluations" AMA, 6th Edition (1986); to amounts somewhat larger since the nephrotoxicity potential is reduced in these compositions.

The nephrotoxicity-inhibiting effects of the polyanionic polymers of this invention were demonstrated in a rat model of gentamicin-induced nephrotoxicity. A ten day period of gentamicin dosing (50mg/kg/day) reproducibly results in severe nephrotoxicity as shown by increased serum urea nitrogen (BUN) and creatinine levels as well as by microscopic kidney evaluation. Coadministering a polymer of this invention prevented or significantly ameliorated gentamicin-induced nephrotoxicity.

EXAMPLE I

Groups consisting of 4 male F344 rats received daily subcutaneous doses of 50 mg/kg of gentamicin along with one of the following compounds administered approximately 5 minutes before the aminoglycoside: 100 or 400 mg/kg of polyacrylic acid (mol.wt. ca. 5,100; and which was substantially neutralized with sodium hydroxide), 100 or 400 mg/kg of DAXAD ® (mol. wt. 15,000–19,000). Separate control groups received either 50 mg/kg of gentamicin or saline. Daily doses were equally divided and administered 6 hours apart for 10 consecutive days. Serum urea nitrogen (BUN) and creatinine, along with gross and microscopic evaluation of the kidneys were conducted at the end of the study to evaluate nephrotoxicity.

TEST MATERIALS

The test materials are available in commerce.

a. Gentamicin (Gentamicin Sulfate Injection, USP, Elkins-Sinn, Inc., Cherry Hill, N.J.)

b. Polyacrylic acid which was substantially neutralized with sodium hydroxide to about pH 7 (mol. wt. approximately 5100)

c. DAXAD 30S ® (sodium salt of polymethacrylic acid with average mol. wt. in range of 15,000-19,000; W. R. Grace and Co.) For dosing purposes, solutions were prepared using sterile water. Nominal concentrations of these dosing solutions were: 25 mg gentamicin activity per ml, 31.25 mg/ml for both polyacrylic acid and DAXAD ® solutions. The aminoglycoside and nephrotoxicity inhibitor solutions were administered twice daily for 10 days with the inhibitor given 5 minutes prior to the gentamicin dose. The various dose groups are presented in Table 1.

TABLE 1

Test Dose Groups

| Group No. | Test Material | Dose Level (mg/kg) | Concentration (mg/kg) | Dose Volume (ml/kg) |
|---|---|---|---|---|
| 1 | saline/saline | — | — | 6.4/1.0 |
| 2 | saline/gentamicin | —/25 | —/25 | 6.4/1.0 |
| 3 | polyacrylic acid/gentamicin | 50/25 | 31.25/25 | 1.6/1.0 |
| 4 | polyacrylic acid/gentamicin | 200/25 | 31.25/25 | 6.4/1.0 |
| 5 | DAXAD/gentamicin | 50/25 | 31.25/25 | 1.6/1.0 |
| 6 | DAXAD/gentamicin | 200/25 | 31.25/25 | 6.4/1.0 |

The 50 mg/kg/day dose of gentamicin (Group No. 2) resulted in severe nephrotoxicity characterized by degeneration, necrosis and regeneration of cortical proximal tubule cells along with significant elevations in BUN and creatinine. Prior administration of polyacrylic acid or DAXAD ® at both dose levels prevented or significantly reduced gentamicin-induced nephrotoxicity. Vacuole formation in proximal tubule cells was apparent in the kidneys of rats given polyacrylic acid and DAXAD ®. No changes in kidney function were observed however. Vacuole formation was less frequent in DAXAD ®treated rats. No significant clinical signs of toxicity were observed in any of the treatment groups.

What is claimed is:

1. A method for inhibiting nephrotoxicity in a patient due to administration thereto of an aminoglycoside antibiotic comprising the administration to said patient of an inhibitory dose of a water-soluble polyanionic organic acid polymer selected from the group of polymers consisting of:
   a. homopolymers comprised of polyacrylic acid, polymethacrylic acid, polyvinylsulfonic acid and polymaleic acid;
   b. copolymers comprised of any two of polyacrylic acid, polymethacrylic acid, polyvinylsulfonic acid and polymaleic acid;
   c. copolymers comprised of polyacrylic acid, polymethacrylic acid, polyvinylsulfonic acid and polymaleic acid, and a lesser amount of a pharmaceutically acceptable comonomer; wherein the organic acid polymer has a molecular weight of from about 1,000 to 50, 000; and is in a pharmaceutically acceptable salt form, and solvates thereof.

2. The method of claim 1 wherein the polyanionic polymer is administered to a patient concurrently with administration of a therapeutically effective amount of an aminoglycoside antibiotic.

3. The method of claim 2 wherein the aminoglycoside and the polyanionic polymer are coadministered in a pharmaceutically acceptable carrier.

4. The method of claim 1 wherein the polyanionic polymer has a molecular weight of from about 1,000 to about 20,000.

5. The method of claim 4 wherein the polyanionic polymer is comprised of polyacrylic acid or polymethacrylic acid or a pharmaceutically acceptable salt thereof, and is present in an amount of at least 0.005 moles per mole of aminoglycoside antibiotic.

6. The method of claim 2 wherein the aminoglycoside is gentamicin or amikacin.

7. An aminoglycoside parenteral composition with reduced nephrotoxicity comprising:
   a. an aminoglycoside or a pharmaceutically acceptable salt thereof; and
   b. at least 0.002 moles, per mole of aminoglycoside, of at least one water-soluble polyanionic organic acid polymer selected from the group of polymers consisting of:
      1. homopolymers comprised of polyacrylic acid, polymethacrylic acid, polyvinylsulfonic acid and polymaleic acid;
      2. copolymers comprised of any two of polyacrylic acid, polymethacrylic acid, polysulfonic acid and polymaleic acid;
      3. copolymers comprised of polyacrylic acid, polymethacrylic acid, polyvinylsulfonic acid, and polymaleic acid, and a lesser amount of a pharmaceutically acceptable comonomer;
   wherein the polyanionic organic acid polymer has a molecular weight of from about 1,000 to 50,000; and is in a pharmaceutically acceptable salt form and solvates thereof, and
   c. a pharmaceutically acceptable solvent, vehicle or carrier.

8. The composition of claim 7 wherein the water-soluble polyanionic polymer has a molecular weight of from about 1,000 to about 20,000.

9. The composition of claim 7 wherein the water-soluble polyanionic polymer is polyacrylic acid or polymethacrylic acid in a pharmaceutically acceptable salt from, and is present in an amount of at least 0.005 moles per mole of aminoglycoside antibiotic.

10. The composition of claim 7 wherein the aminoglycoside is gentamicin or amikacin.

11. The composition of claim 9 wherein the aminoglycoside is gentamicin or amikacin.

12. The composition of claim 7 in unit dosage form.

13. The composition of claim 9 in unit dosage form.

14. The composition of claim 9 in unit dosage form.

15. The composition of claim 10 in unit dosage form.

16. The composition of claim 11 in unit dosage form.

* * * * *